US012564600B2

(12) United States Patent
Jiang et al.

(10) Patent No.: US 12,564,600 B2
(45) Date of Patent: Mar. 3, 2026

(54) SYSTEM FOR ENHANCING THERAPEUTIC COMPLIANCE OF THE ANTI-CANCER COMPOUND E7766

(71) Applicant: Eisai R&D Management Co., Ltd., Tokyo (JP)

(72) Inventors: Rongrong Jiang, Medford, MA (US); Vaishali Dixit, Cambridge, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 838 days.

(21) Appl. No.: 17/597,199

(22) PCT Filed: Jul. 1, 2020

(86) PCT No.: PCT/US2020/040515
§ 371 (c)(1),
(2) Date: Dec. 29, 2021

(87) PCT Pub. No.: WO2021/003279
PCT Pub. Date: Jan. 7, 2021

(65) Prior Publication Data
US 2022/0304982 A1     Sep. 29, 2022

Related U.S. Application Data

(60) Provisional application No. 62/869,389, filed on Jul. 1, 2019.

(51) Int. Cl.
*A61K 31/7084*     (2006.01)
*A61K 31/496*      (2006.01)
*A61K 45/06*       (2006.01)
*A61P 35/00*       (2006.01)

(52) U.S. Cl.
CPC ........ *A61K 31/7084* (2013.01); *A61K 31/496* (2013.01); *A61K 45/06* (2013.01); *A61P 35/00* (2018.01)

(58) Field of Classification Search
CPC ............................ A61P 35/00; A61K 31/7084
USPC ........................................................ 514/236
See application file for complete search history.

(56) References Cited

U.S. PATENT DOCUMENTS

| | | | |
|---|---|---|---|
| 10,246,480 B2 * | 4/2019 | Kim ........................ | C07H 21/00 |
| 2018/0237468 A1 * | 8/2018 | Kim .................... | A61K 31/7084 |
| 2024/0207233 A1 | 6/2024 | Oshima et al. | |

FOREIGN PATENT DOCUMENTS

| | | |
|---|---|---|
| EP | 2446893 A1 | 5/2012 |
| JP | 2015-516423 A | 6/2015 |
| JP | 2019-052192 A | 4/2019 |
| JP | 2019-512233 A | 5/2019 |
| RU | 2721953 C2 | 5/2020 |

| | | |
|---|---|---|
| WO | 2013169616 A1 | 11/2013 |
| WO | 2016141185 A1 | 9/2016 |
| WO | 2017156356 A1 | 9/2017 |
| WO | 2018152450 A1 | 8/2018 |
| WO | 2019/078920 A1 | 4/2019 |

OTHER PUBLICATIONS

Durmus et al., The impact of Organic Anion-Transporting Polypeptides (OATPs) on disposition and toxicity of antitumor drugs: Insights from knockout and humanized mice, Drug Resistance Updates, 2016, vol. 27, pp. 72-88. (Year: 2016).*

Huang et al., Organic Anion Transporting Polypeptides and Effect Thereof on Absorption, Distribution and Clearance of Pharmaceuticals, Pharmacy Today, 2010, vol. 20(12), English abstract. (Year: 2010).*

Notification of the First Office Action issued on Jun. 26, 2023, by the Chinese Patent Office in corresponding Chinese Patent Application No. 202080061033.0 and an English translation of the Office Action, pp. 1-18. (Year: 2023).*

Huang et al. (Organic Anion Transporting Polypeptides and Effect Thereof on Absorption, Distribution and Clearance of Pharmaceuticals, Pharmacy Today, 2010, vol. 20(12) pp. 1-4 (Year: 2010).*

International Search Report (PCT/ISA/210) and Written Opinion (PCT/ISA/237) mailed on Oct. 16, 2020, by the European Patent Office as the International Searching Authority for International Application No. PCT/US2020/040515.

Jiang et al., "Prediction of transporter-mediated drug-drug interactions and phenotyping of hepatobiliary transporters involved in the clearance of E7766, a novel macrocycle-bridged dinucleotide", DMD Fast Forward, Published on Dec. 18, 2020, 57 pages.

US Department of Health and Human Services, Food and Drug Administration, Center for Drug Evaluation and Research, "In Vitro Drug Interaction Studies—Cytochrome P450 Enzyme- and Transporter-Mediated Drug Interactions Guidance for Industry" Jan. 2020, 46 pages.

Bao, et al., "Discovery and Preclinical Development of E7766, a Novel Sting Agonist for Cancer Immunotherapy with a Superior Profile over a Leading Reference Compound", Journal for ImmunoTherapy of Cancer, vol. 6, Supplement 1, Retrieved from STN Database accession No. EMB-627524689, XP055737829, Nov. 1, 2018, p. 598.

Berge, et al., "Pharmaceutical Salts", Journal of Pharmaceutical Sciences, vol. 66, No. 1, Jan. 1977, pp. 1-19.

Karlgren, et al., "Classification of Inhibitors of Hepatic Organic Anion Transporting Polypeptides (OATPS): Influence of Protein Expression on Drug-drug Interactions", Journal of Medicinal Chemistry, vol. 55, No. 10, 2012, pp. 4740-4763.

(Continued)

*Primary Examiner* — Jeffrey H Murray
*Assistant Examiner* — Rilla Marie Samsell
(74) *Attorney, Agent, or Firm* — BUCHANAN INGERSOLL & ROONEY PC

(57)                    ABSTRACT

Disclosed herein are systems and methods for reducing medication error caused by a drug-drug interaction between Compound 1 (E7766) and an OATP inhibitor. Methods for monitoring the exposure of Compound 1 in a patient and preventing overexposure of Compound 1 in a patient are also disclosed.

12 Claims, 7 Drawing Sheets

(56)           References Cited

OTHER PUBLICATIONS

Varma, et al., "Predicting Clearance Mechanism in Drug Discovery: Extended Clearance Classification System (ECCS)", Pharmaceutical Research, vol. 32, No. 12, Jul. 9, 2015, pp. 3785-3802.

Huang et al. "Organic Anion Transporting Polypeptides and Effect Thereof on Absorption, Distribution and Clearance of Pharmaceuticals", Pharmacy Today, vol. 20, Issue 12, pp. 1-4, with English Abstract.

Notification of the First Office Action issued on Jun. 26, 2023, by the Chinese Patent Office in corresponding Chinese Patent Application No. 202080061033.0, and an English Translation of the Office Action. (18 pages).

English translation of the Russian Search Report Completed on Apr. 2, 2024 by the Federal Service on Intellectual Property Federal State Budgetary Enterprise "Federal Institute of Industrial Property" (FIPS) in corresponding Russian Patent Application No. 2022101963, 2 page.

Office Action (Notice of Reasons for Rejection) issued on Dec. 17, 2024, by the Japanese Patent Office in corresponding Japanese Patent Application No. 2021-578078, and an English Translation of the Office Action. (6 pages).

* cited by examiner

A

B

FIG. 1C and FIG. 1D
C
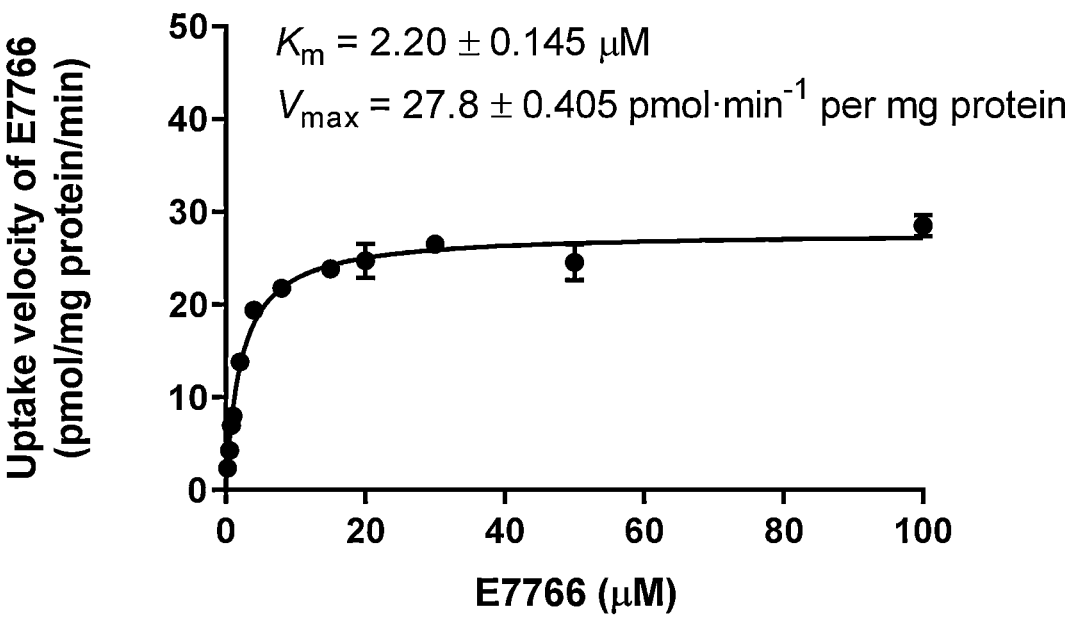
OATP1B1-specific Uptake of E7766
$K_m = 2.20 \pm 0.145 \ \mu M$
$V_{max} = 27.8 \pm 0.405 \ \text{pmol·min}^{-1}$ per mg protein
D
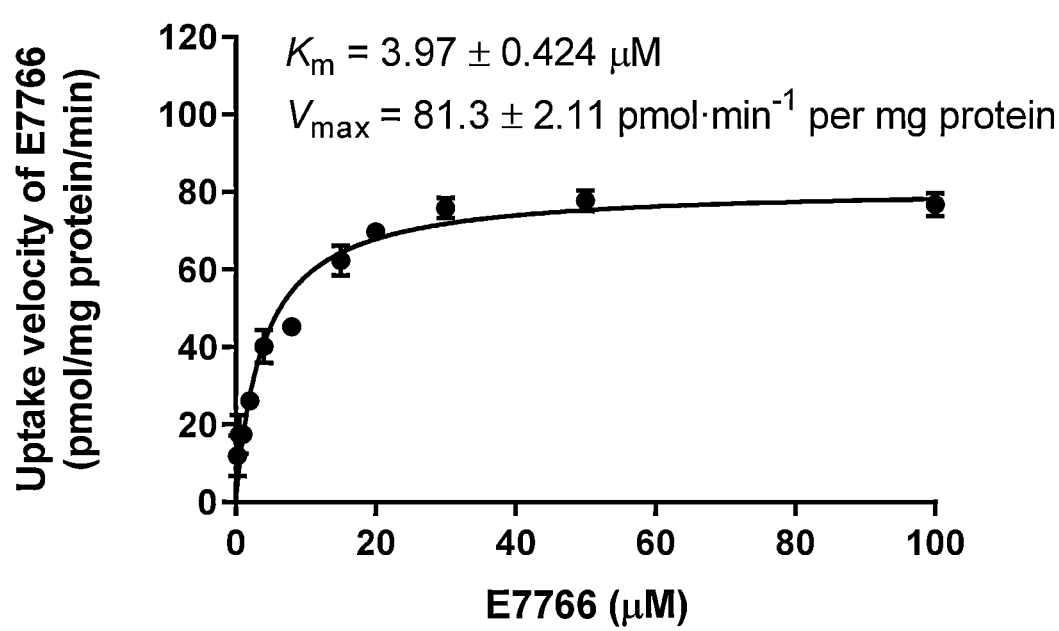
OATP1B3-specific Uptake of E7766
$K_m = 3.97 \pm 0.424 \ \mu M$
$V_{max} = 81.3 \pm 2.11 \ \text{pmol·min}^{-1}$ per mg protein

SYSTEM FOR ENHANCING THERAPEUTIC COMPLIANCE OF THE ANTI-CANCER COMPOUND E7766

CROSS-REFERENCE TO RELATED APPLICATIONS

This application claims the benefit of U.S. Provisional Patent Application No. 62/869,389, which was filed on Jul. 1, 2019. That application is incorporated by reference as if fully rewritten herein.

BACKGROUND

Understanding the mechanism and kinetics of clearance of new chemical entities in drug development is important to ensure safe and efficacious patient exposure to new chemical entities and avoid clinically adverse interactions that may be caused by co-administration with other drugs. Compound 1, which is the diammonium salt of E7766, shown below, has been reported for use in treatment of cancer. See, for example, U.S. Pat. No. 10,246,480, which is incorporated by reference herein.

$_{31}.0^{4,8}.0^{7,12}.0^{19,24}.0^{23,27}$]dotetraconta-5,7,9,11,15,19,21,23, 25-nonaene-34,39-dione. If there exist any discrepancies as between this chemical name and the structure given above, the structure given above will control.

BRIEF SUMMARY

To assist in clinical trial preparations, we have employed pre-clinical models to gauge the clearance of Compound 1 both alone and when potentially affected by drug-drug interactions. While not wishing to be bound by theory, based on our review of the compound, we concluded that the compound would have low Log P (<1), low permeability ($<1\times10^{-6}$ cm/sec), pKa between 3-4 and MW >600. This would cause Compound 1 to be classified as Class 3B according to the Extended Clearance Classification System. Compounds in that class are predominantly cleared by active uptake followed by elimination in bile or urine.

E7766 is presented below. Compound 1, which is the diammonium salt of E7766, has a molecular weight of 780.7, a measured pKa of 3.41, a measured Log D of 1.31, a PSA of 200, solubility of 150 µmol/L, Papp value of $0.36\times10^6$ cm/s, and is ECCS Class 3B using the scale (E7766)

E7766 is also referred to as (1R,3R,15E,28R,29R,30R, 31R,34R,36R,39S,41R)-29,41-Difluoro-34,39-bis(sulfa-nyl)-2,33,35,38,40,42-hexaoxa-4,6,9,11,13,18,20,22,25,27-decaaza-34$\lambda^5$,39$\lambda^5$-diphosphaoctacyclo [28.6.4.1$^{3,36}$.1$^{28,}$ reported in Varma, et al., Pharm Res (2015) 32:3785-3802, which is incorporated by reference herein. In the examples reported herein, Compound 1, the diammonium salt, was used. Typically different lots were used for different studies.

(E7766)

An embodiment provides a system for reducing medication error and enhancing therapeutic compliance of an individual suffering from cancer, comprising at least one container, said container including an amount of a pharmaceutical composition comprising E7766 or a pharmaceutically acceptable salt thereof (E7766)

and at least an advisory accompanying said container, said advisory comprising prescribing information comprising information on potential drug-drug interaction, wherein the information on potential drug-drug interaction comprises information indicating that administration of the pharmaceutical composition leads to a potentially different effect for an individual receiving treatment with organic anion transporting polypeptide inhibitor than would be expected for an individual not receiving an organic anion transporting polypeptide inhibitor. In a further embodiment the organic anion transporting polypeptide inhibitor inhibits an organic anion transporting polypeptide selected from OATP1B1, OATP1B3, and a combination of OATP1B1 and OATP1B3.

In further embodiments reference to "OATP" is limited to OATP1B1 and/or OATP1B3 inhibitors.

In a further embodiment the information on potential drug-drug interaction indicates that the organic anion transporting polypeptide inhibitor and the pharmaceutical composition should not be coadministered. In a further embodiment the information on potential drug-drug interaction indicates that one or both of the organic anion transporting polypeptide inhibitor and the pharmaceutical composition should be administered in a lower dose and/or less frequently than if either were administered without the other.

In some embodiments, dosage of the pharmaceutical composition is decreased by 5%, 10%, 15%, 20%, 25%, 30%, 35%, 40%, 45%, 50%, 55%, 60%, 65%, 70%, 75%, 80%, 85%, 90%, or 95%. In further embodiments, dosage of the pharmaceutical composition is decreased by 5%-75%; decreased by 10%-50%; or decreased by 20%-40%. In some embodiments, dosage of the OATP inhibitor is decreased by 5%, 10%, 15%, 20%, 25%, 30%, 35%, 40%, 45%, 50%, 55%, 60%, 65%, 70%, 75%, 80%, 85%, 90%, or 95%. In further embodiments, dosage of the OATP inhibitor is decreased by 5%-75%; decreased by 10%-50%; or decreased by 20%-40%.

In a further embodiment of the above system, the organic anion transporting polypeptide inhibitor is selected from the group consisting of fimasartan, clarithromycin, rifampin, clopidogrel, eslicarbazepine, CP-778875, isavuconazole, itraconazole, ombitasvir, asunaprevir, boceprevir, daclatasvir, dasabuvir, elbasvir, faldaprevir, glecaprevir, grazoprevir, letermovir, ombitasvir, paritaprevir, pibrentasvir, trimethoprim, ritonavir, simeprevir, sofosbuvir, telaprevir, velpatasvir, voxilaprevir, lopinavir, peficitinib, quercetin, tipranavir, metformin, diltiazem, sacubitril, valsartan, furosemide, gemfibrozil, eluxadoline, cyclosporine, tacrolimus, eltrombopag, grapefruit juice, ursodeoxycholic acid, milk thistle (*Silybum marianum*), emtricitabine, tenofovir, vercirnon (GSK1605786), telmisartan, epigallocatechin gallate, ezetimibe, amlodipine, obeticholic acid, omega-3 carboxylic acids, idelalisib, baicalin, empagliflozin, elvitegravir and cobicistat.

A further embodiment provides a method of preventing overexposure of E7766 or a pharmaceutically acceptable salt thereof in a patient selected for treatment with E7766 or a pharmaceutically acceptable salt thereof, comprising administering E7766 or a pharmaceutically acceptable salt thereof to said patient when said patient is not also being administered a drug that is an OATP1B1 or OATP1B3 inhibitor.

A further embodiment provides a method of preventing overexposure of E7766 or a pharmaceutically acceptable salt thereof in a patient selected for treatment with E7766 or a pharmaceutically acceptable salt thereof, comprising administering E7766 or a pharmaceutically acceptable salt thereof to said patient when said patient is being administered an amount of a drug that is an OATP1B1 or OATP1B3 inhibitor that is less than an amount of the OATP1B1 or OATP1B3 inhibitor that said patient would be administered in the absence of administration of E7766 or a pharmaceutically acceptable salt thereof.

A further embodiment provides a method of preventing overexposure of E7766 or a pharmaceutically acceptable salt thereof in a patient selected for treatment with E7766 or a pharmaceutically acceptable salt thereof, comprising administering E7766 or a pharmaceutically acceptable salt thereof to a patient who is being administered an amount of a drug that is an OATP1B1 or OATP1B3 inhibitor, comprising administering to said patient an amount of E7766 or a pharmaceutically acceptable salt thereof that is less than an amount of E7766 or a pharmaceutically acceptable salt thereof that said patient would be administered in the absence of administration of OATP1B1 inhibitor or OATP1B3 inhibitor.

In some embodiments the E7766 or a pharmaceutically acceptable salt thereof is administered after at least 1 day following administration of said drug; after at least 2 days following administration of said drug; after at least 3 days following administration of said drug; after at least 4 days following administration of said drug; after at least 5 days following administration of said drug; after at least 6 days following administration of said drug; after at least 7 days following administration of said drug; after at least 2 weeks following administration of said drug; after at least 3 weeks following administration of said drug; or after at least 1 month following administration of said drug.

In embodiments of the method reported herein said drug may be selected from the group consisting of fimasartan, clarithromycin, rifampin, clopidogrel, eslicarbazepine, CP-778875, isavuconazole, itraconazole, ombitasvir, asunaprevir, boceprevir, daclatasvir, dasabuvir, elbasvir, faldaprevir, glecaprevir, grazoprevir, letermovir, ombitasvir, paritaprevir, pibrentasvir, trimethoprim, ritonavir, simeprevir, sofosbuvir, telaprevir, velpatasvir, voxilaprevir, lopinavir, peficitinib, quercetin, tipranavir, metformin, diltiazem, sacubitril, valsartan, furosemide, gemfibrozil, eluxadoline, cyclosporine, tacrolimus, eltrombopag, grapefruit juice, ursodeoxycholic acid, milk thistle (*Silybum marianum*), emtricitabine, tenofovir, vercirnon (GSK1605786), telmisartan, epigallocatechin gallate, ezetimibe, amlodipine, obeticholic acid, omega-3 carboxylic acids, idelalisib, baicalin, empagliflozin, elvitegravir and cobicistat.

Further embodiments provide a method of preventing overexposure of E7766 or a pharmaceutically acceptable salt thereof in a patient selected for treatment with E7766 or a pharmaceutically acceptable salt thereof, comprising monitoring the exposure of E7766 or a pharmaceutically acceptable salt thereof to said patient and maintaining said exposure to a value below 12,800 μg E7766 or a pharmaceutically acceptable salt thereof per 100 kg patient body weight; maintaining said exposure to a value below 9,600 μg E7766 or a pharmaceutically acceptable salt thereof per 100 kg patient body weight; maintaining said exposure to a value below 6,400 μg E7766 or a pharmaceutically acceptable salt thereof per 100 kg patient body weight; maintaining said exposure to a value below 3,200 μg E7766 or a pharmaceutically acceptable salt thereof per 100 kg patient body weight; maintaining said exposure to a value below 2,400 μg E7766 or a pharmaceutically acceptable salt thereof per 100 kg patient body weight; maintaining said exposure to a value below 2,000 μg E7766 or a pharmaceutically acceptable salt thereof per 100 kg patient body weight; maintaining said exposure to a value below 1,750 μg E7766 or a pharmaceutically acceptable salt thereof per 100 kg patient body weight; maintaining said exposure to a value below 1,600 μg E7766 or a pharmaceutically acceptable salt thereof per 100 kg patient body weight; maintaining said exposure to a value below 1,200 μg E7766 or a pharmaceutically acceptable salt thereof per 100 kg patient body weight; maintaining said exposure to a value below 800 μg E7766 or a pharmaceutically acceptable salt thereof per 100 kg patient body weight; maintaining said exposure to a value below 600 μg E7766 or a pharmaceutically acceptable salt thereof per 100 kg patient body weight; maintaining said exposure to a value below 300 μg E7766 or a pharmaceutically acceptable salt thereof per 100 kg patient body weight; maintaining said exposure to a value below 150 μg E7766 or a pharmaceutically acceptable salt thereof per 100 kg patient body weight; maintaining said exposure to a value below 75 μg E7766 or a pharmaceutically acceptable salt thereof per 100 kg patient body weight; maintaining said exposure to a value below 50 μg E7766 or a pharmaceutically acceptable salt thereof per 100 kg patient body weight; or maintaining said exposure to a value below 25 μg E7766 or a pharmaceutically acceptable salt thereof per 100 kg patient body weight. In some embodiments exposure to E7766 or a pharmaceutically acceptable salt thereof as recited in this paragraph is performed in a patient administered an OATP1B1 inhibitor and/or OATP1B3 inhibitor.

In some methods the maintaining step is comprises decreasing a dosage amount of E7766 or a pharmaceutically acceptable salt thereof. This may be decreased, for example, by 5%, 10%, 15%, 20%, 25%, 30%, 35%, 40%, 45%, 50%, 55%, 60%, 65%, 70%, 75%, 80%, 85%, 90%, or 95% of a previous value.

In some methods said exposure is monitored by quantifying the presence of E7766 or a pharmaceutically acceptable salt thereof in said patient's blood. In some methods said exposure is evaluated from said patient's blood plasma.

A further embodiment provides a system or method as set forth herein, wherein said pharmaceutically acceptable salt of E7766 is a diammonium salt of E7766.

A further embodiment provides a method of treating cancer in a patient selected for treatment with E7766 or a pharmaceutically acceptable salt therefor, comprising administering E7766 or a pharmaceutically acceptable salt thereof to said patient, wherein said patient has not received treatment with an organic anion transporting polypeptide (OATP) inhibitor.

A further embodiment provides a method of treating cancer in a patient selected for treatment with E7766 or a pharmaceutically acceptable salt therefor, comprising administering E7766 or a pharmaceutically acceptable salt thereof to said patient, wherein said patient has previously received an OATP inhibitor or is still receiving an OATP inhibitor, and concomitantly ceasing or reducing administration of said OATP inhibitor to eliminate or reduce the frequency of related adverse events.

A still further embodiment provides a method of treating cancer in a patient selected for treatment with E7766 or a pharmaceutically acceptable salt therefor, comprising administering E7766 or a pharmaceutically acceptable salt thereof to said patient, wherein said patient has previously received an OATP inhibitor or is still receiving an OATP inhibitor, and concomitantly ceasing or reducing administration of said E7766 or a pharmaceutically acceptable salt thereof to eliminate or reduce related adverse events.

In some embodiments the OATP inhibitor is selected from the group consisting of: fimasartan, clarithromycin, rifampin, clopidogrel, eslicarbazepine, CP-778875, isavuconazole, itraconazole, ombitasvir, asunaprevir, boceprevir, daclatasvir, dasabuvir, elbasvir, faldaprevir, glecaprevir, grazoprevir, letermovir, ombitasvir, paritaprevir, pibrentasvir, trimethoprim, ritonavir, simeprevir, sofosbuvir, telaprevir, velpatasvir, voxilaprevir, lopinavir, peficitinib, quercetin, tipranavir, metformin, diltiazem, sacubitril, valsartan, furosemide, gemfibrozil, eluxadoline, cyclosporine, tacrolimus, eltrombopag, grapefruit juice, ursodeoxycholic acid, milk thistle (*Silybum marianum*), emtricitabine, tenofovir, vercirnon (GSK1605786), telmisartan, epigallocatechin gallate, ezetimibe, amlodipine, obeticholic acid, omega-3 carboxylic acids, idelalisib, baicalin, empagliflozin, elvitegravir and cobicistat.

In some embodiment E7766 or a pharmaceutically acceptable salt thereof is administered after at least 1 day following administration of the OATP inhibitor. In some embodiments E7766 or a pharmaceutically acceptable salt thereof is administered after at least 2 day following administration of the OATP inhibitor. In some embodiments E7766 or a pharmaceutically acceptable salt thereof is administered after at least 3 day following administration of the OATP inhibitor. In some embodiments E7766 or a pharmaceutically acceptable salt thereof is administered after at least 4 day following administration of the OATP inhibitor. In some embodiments E7766 or a pharmaceutically acceptable salt thereof is administered after at least 5 day following administration of the OATP inhibitor. In some embodiments E7766 or a pharmaceutically acceptable salt thereof is administered after at least 6 day following administration of the OATP inhibitor. In some embodiments E7766 or a pharmaceutically acceptable salt thereof is administered after at least 7 days following administration of the OATP inhibitor. In some embodiments E7766 or a pharmaceutically acceptable salt thereof is administered after at least 2 weeks following administration of the OATP inhibitor. In some embodiments E7766 or a pharmaceutically acceptable salt thereof is administered after at least 3 weeks following administration of the OATP inhibitor. In some embodiments E7766 or a pharmaceutically acceptable salt thereof is administered after at least 1 month following administration of the OATP inhibitor. In some embodiments the patient is still receiving the OATP inhibitor. In embodiments as recited above the OATP inhibitor is typically OATP1B1 and/or OATP1B3.

BRIEF DESCRIPTION OF THE FIGURES

FIG. 1A through FIG. 1D show results of in vitro hepatobiliary transporter phenotyping and kinetic studies of Compound 1.

DETAILED DESCRIPTION OF EMBODIMENTS

Figure 1A:
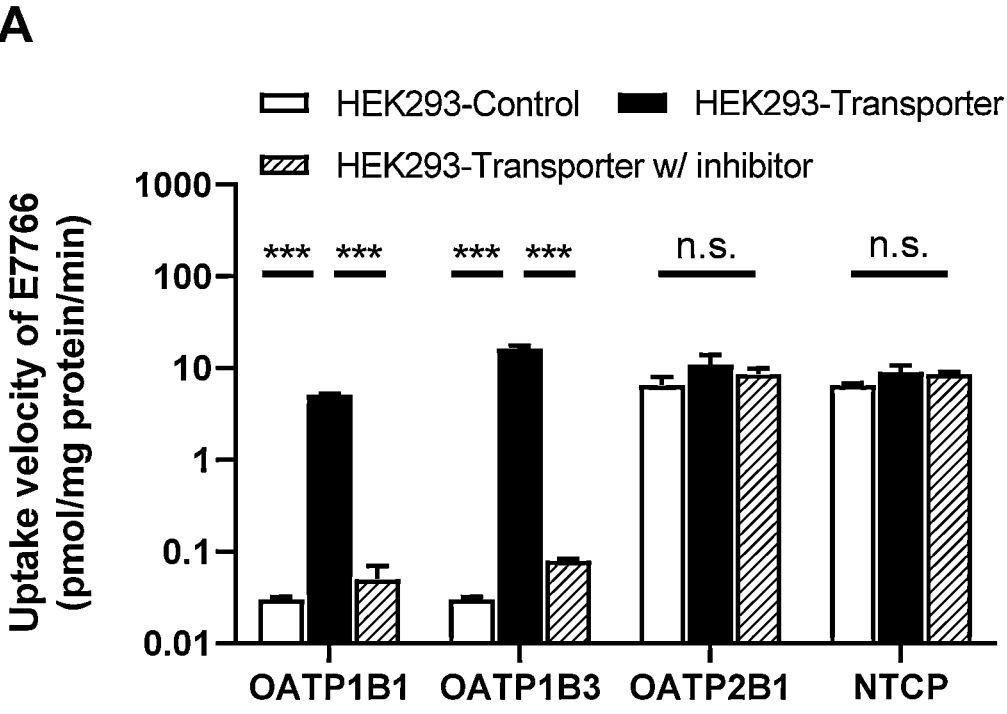

We studied pharmacokinetics and disposition of Compound 1 in in vitro systems as well as in in vivo preclinical species. Pharmacokinetics in bile duct cannulated rat and dog showed that Compound 1 was predominantly excreted unchanged in the bile (>80%) and to a minor extent in urine (<20%). Uptake studies with human hepatocytes showed temperature-dependent active uptake, which could be inhibited by Rifampin but not by tetraethylammonium indicate organic anion transporting polypeptide (OATP) involvement in the elimination of Compound 1. Further studies with HEK293 cells overexpressing human OATP1B1 and OATP1B3 confirmed that Compound 1 is a substrate of OATP1B1 and OATP1B3.

In vitro studies in multidrug resistance-associated protein 2 (MRP2) expressing vesicles demonstrated Compound 1 is a substrate of the biliary efflux transporter MRP2. Pharmacokinetics of Compound 1 was also assessed in humanized OATP1B1/1B3, Oatp1a/1b knockout or wild-type mice. In wild-type mice, an increase (5.4-fold) in plasma exposure of Compound 1 was observed in the presence of rifampin, whereas liver exposures of Compound 1 were comparable in the presence or absence of rifampin in the wild type mice. Plasma concentration of Compound 1 increased 4.5-fold in the presence of rifampin in humanized OATP1B1/1B3 mice. These preclinical results predict that OATP-mediated hepatic uptake is the rate limiting step in the clearance of Compound 1, and these preclinical results also predict that the inhibition of OATPs in the clinic will lead to a significant elevation of systemic exposure of Compound 1.

Those of skill in the art will recognize that where substituents bound to the phosphorous atoms ($P_1$,$P_2$) have both single and double bonds, they may be susceptible to tautomerization.

For example, the compounds may tautomerize at equilibrium. One example is shown below:

Such tautomers should be considered to be within the scope of the claims. A structural representation of either tautomer for a given compound will represent the same compound.

Methods of Treatment

In some embodiments, E7766 or a pharmaceutically acceptable salt is administered to a patient in need of treatment. In some embodiments, the administered compound is provided as an $NH_4$ salt, a free acid, or a pharmaceutically acceptable salt thereof. In some embodiments, the compound is provided as an $NH_4$ salt. When E7766 is provided as an $NH_4$ salt, the compound is referred to as Compound 1.

Dosages

The optimal dose for treatment of cancer can be determined empirically for each individual using known methods and will depend upon a variety of factors, including the activity of the agents; the age, body weight, general health, gender and diet of the individual; the time and route of administration; and other medications the individual is taking. Optimal dosages may be established using routine testing and procedures that are well known in the art. Administration of the above compounds may be by any suitable route.

A "drug-drug interaction" as used herein refers to pharmacokinetic or pharmacodynamics effects that may occur when two or more drugs are co-administered. Such effects typically do not arise when drugs are administered alone (i.e, not in the presence of other drugs). Non-limiting examples of pharmacokinetic drug-drug interaction effects may include, for example, changes in the absorption, distribution, metabolisis or excretion of one or both co-administered drugs. Non-limiting examples of pharmacodynamics drug-drug interaction effects may include, for example, one drug interfering (e.g., competitively or allosterically) with another drug at a protein (or receptor) binding site, or interfering indirectly through binding of a protein (or receptor) in a related biological pathway. Non-limiting examples of drug-drug interactions may include expected side effects, unexpected side effect, clinically adverse events and contraindications, all of which may be managed during administration of the drugs potentially involved in a drug-drug interaction.

"Pharmaceutically acceptable salt" as used herein refers to acid addition salts or base addition salts of the compounds in the present disclosure. A pharmaceutically acceptable salt is any salt which retains the activity of the parent compound and does not impart any unduly deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydrochloride, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Sodium salts and potassium salts may also be prepared.

Embodiments may be diammonium salts of E7766. Pharmaceutically acceptable salts may be derived from amino acids including, but not limited to, cysteine. Methods for producing compounds as salts are known to those of skill in the art (see, e.g., Stahl et al., Handbook of Pharmaceutical Salts: Properties, Selection, and Use, Wiley-VCH; Verlag Helvetica Chimica Acta, Zurich, 2002; Berge et al., J. Pharm. Sci. 66: 1, 1977).

An "effective amount" or "therapeutically effective amount" of a therapeutic agent is an amount sufficient to provide an observable therapeutic benefit compared to cancer left untreated in a subject or patient.

Active agents as reported herein can be combined with a pharmaceutically acceptable carrier to provide pharmaceutical formulations thereof. The particular choice of carrier and formulation will depend upon the particular route of administration for which the composition is intended.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, sorbic acid, potassium sorbate, partial glyceride mixtures of saturated vegetable fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

The compositions of the present invention may be suitable for parenteral, oral, inhalation spray, topical, rectal, nasal, buccal, vaginal, intravesicular, intravesical, intratumoral or implanted reservoir administration, etc. In some embodiments, the formulation comprises ingredients that are from natural or non-natural sources. In some embodiments, the formulation or carrier may be provided in a sterile form. Non-limiting examples of a sterile carrier include endotoxin-free water or pyrogen-free water. Compositions may be administered through intravesicular, intravesical, or intratumoral administration.

The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids and their glyceride derivatives are useful in the preparation of injectables, as are natural pharmaceutically acceptable oils, such as olive oil or castor oil, especially in their polyoxy-ethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents that are commonly used in the manufacture of pharmaceutically acceptable solid, liquid, or other dosage forms may also be used for the purposes of formulation.

For oral administration, a compound or salt may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient may be combined with emulsifying and suspending agents. If desired, certain sweetening, flavoring or coloring agents may also be added. In addition preservatives may also be added. Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

"Immediate-release" is meant to include a conventional release, in which release of the drug starts immediately after administration. As used herein, the term "immediate release" includes dosage forms that allow the drug to dissolve in the gastrointestinal contents, with no intention of delaying or prolonging the dissolution or absorption of the drug. The objective is for the drug to be released rapidly after administration, for example for it to be possible to release at least 80% of the drug within approximately 30 minutes after commencement of dissolution in a dissolution test.

"Sustained-release" or "extended-release" includes dosage forms whose drug-release characteristics of time course and/or location are chosen to accomplish therapeutic or convenience objectives not offered by conventional dosage forms such as a solution or an immediate release dosage form.

The term "steady-state" means that a plasma level for a given active agent has been achieved and which is maintained with subsequent doses of the active agent at a level which is at or above the minimum effective therapeutic level and is below the minimum toxic plasma level for a given active agent.

The term "dose range" as used herein refers to an upper and a lower limit of an acceptable variation of the amount of agent specified. Typically, a dose of an agent in any amount within the specified range can be administered to patients undergoing treatment.

The term "treat" is used herein to mean to relieve, reduce or alleviate at least one symptom of a disease in a subject. For example, in relation to cancer, the term "treat" may mean to arrest, delay the onset (i.e., the period prior to clinical manifestation of a disease or symptom of a disease) and/or reduce the risk of developing or worsening a symptom of cancer. The term "protect" is used herein to mean prevent delay or treat, or all, as appropriate, development or continuance or aggravation of symptoms of cancer in a subject.

The term "subject" or "patient" is intended to include animals, which are capable of suffering from or afflicted with cancer. Examples of subjects or patients include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer.

"Advisory" as used herein may include documentation as part of a regulatory approved pharmaceutical product, including, but not limited to a product label or product insert. Such documentation may include instructions, precautions or warnings to a patient or prescribing physician, for example, in one or more of the Drug Interactions, Clinical Pharmacology, Dosage and Administration, Warnings and Precautions, Contraindications, or Boxed Warnings sections.

The term "about" or "approximately" usually means within 20%, more preferably within 10%, and most preferably still within 5% of a given value or range. Alternatively, especially in biological systems, the term "about" means approximately within a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein.

Exemplary cell proliferative disorders that may be treated using one or more compounds disclosed herein include, but are not limited to cancer, a precancer or precancerous condition, and metastatic lesions in tissue and organs in the body. Cell proliferative disorders may include hyperplasia, metaplasia, and dysplasia.

A compound disclosed herein, or a pharmaceutically acceptable salt thereof, may be used to treat or prevent a cell proliferative disorder, or to treat or prevent cancer, in a subject having an increased risk of developing cancer relative to the population at large, or used to identify suitable candidates for such purposes.

Pharmaceutical Formulations and Routes of Administration

Provided herein are pharmaceutical formulations comprising E7766 or a pharmaceutically acceptable salt thereof for the treatment of cancer. The pharmaceutical formulations may additionally comprise a carrier or excipient, stabilizer, flavoring agent, and/or coloring agent.

E7766 or a pharmaceutically acceptable salt thereof may be administered using a variety of routes of administration known to those skilled in the art. Routes of administration include oral administration, intratumoral administration, intravesical administration, and intravesicular administration. In certain embodiments, a pharmaceutical formulation comprising the compound or pharmaceutically acceptable salt thereof may be taken orally in the form of liquid, syrup, tablet, capsule, powder, sprinkle, chewtab, or dissolvable disk. Alternatively, pharmaceutical formulations of the present invention can be administered intravenously or transdermally. Additional routes of administration are known to those skilled in the art (see, e.g., Remington's Pharmaceutical Sciences, Gennaro A. R., Ed., 20th Edition, Mack Publishing Co., Easton, Pa.).

In some embodiments, the compound or pharmaceutically acceptable salt is formulated as a paste, jelly, or suspension. For example, the drug is dissolved, entrapped or suspended in the form of drug particles, microencapsulated particles, or drug-polymer particles in a gelatinous solution or semisolid. An advantage of an oral jelly formulation is that it is easier to administer the drug to patients who have difficulty swallowing tablets, capsules or pills. In certain embodiments, the compound is thoroughly mixed and suspended in an appropriate medium to form a paste or a gel. Additional agents can optionally be mixed to provide flavor during oral administration. Peanut butter or alginate, flavored with raspberry and a sweetener are examples of the many suitable taste masking agents. In various embodiments, the paste or jelly can also be formulated with suitable binders or excipients known in the art for topical administration.

Methods of preparing sustained release formulations in the form of tablets, capsules or pills are known in the art. In some embodiments, the sustained release formulation is prepared by coating the active ingredient of the drug with a polymer, preferably a water-insoluble polymer. For example, a water-insoluble polymer used in the pharmaceutical field as a sustained release coating agent, an enteric coating agent, or a gastric coating agent. The water-insoluble polymer can include, for example, ethyl cellulose, purified shellac, white shellac, aminoalkyl methacrylate copolymer RS, hydroxypropyl methylcellulose phthalate, hydroxypropyl methylcellulose acetate succinate, carboxymethylethylcellulose, cellulose acetate phthalate, methacrylic acid copolymer L, methacrylic acid copolymer LD, methacrylic acid copolymer S, aminoalkyl methacrylate copolymer E, or polyvinyl acetal diethylaminoacetate.

The type, degree of substitution and molecular weight of the water-insoluble polymers can depend on solubility of the active ingredient in water or an alcohol, the desired sustained release level and the like. The water-insoluble polymers can be used either alone or in combination. There can be further incorporated a hydrogenated oil, stearic acid, or cetanol as a coating auxiliary agent, and a middle-chain triglyceride, triacetin, triethyl citrate, or cetanol as a plasticizer.

In some embodiments, the sustained release formulation is a matrix-type tablet or granule. The active ingredient can be coated with up to 3 different types of polymers. These three different types of polymers can include: 1) a water insoluble polymer, such as ethylcellulose; 2) a pH independent gelling polymer, such as hydroxypropyl methylcellulose; and 3) a pH dependent gelling polymer, such as sodium alginate. These three different types of polymers can be used together to attenuate the release rate of the drugs.

Intratumoral Dosages and Regimens

In an embodiment of intratumoral administration, E7766 or a pharmaceutically acceptable salt thereof is administered to a patient in multiple cycles, each lasting 3 weeks. E7766 or a pharmaceutically acceptable salt thereof is administered in the induction cycle (Cycle 1) on days 1, 8 and 15; and administered on day 1 of each subsequent maintenance cycle (Cycle 2 and on). The total dose administered each time may be 25 μg, 50 μg, 75 μg, 150 μg, 300 μg, 600 μg, 1200 μg, or 1750 μg. The dose administered may be in one of the following dosage ranges: 75 μg-1750 μg, 75 μg-1200 μg, 75 μg-600 μg, 75 μg-300 μg, 75 μg-150 μg, 150 μg-1750 μg, 150 μg-1200 μg, 150 μg-600 μg, 150 μg-300 μg, 300 μg-1750 μg, 300 μg-1200 μg, 300 μg-600 μg, 1200 μg-1750 μg, 75 μg-200 g, 75 μg-150 μg, or 100 μg-150 μg.

In an embodiment, E7766 or a pharmaceutically acceptable salt thereof is provided as a solid or concentrated solution and diluted in normal saline to a final volume of 1 mL for intratumoral administration.

In an embodiment, E7766 or a pharmaceutically acceptable salt thereof is provided as an intratumoral administration for treatment of breast cancer (including triple negative breast cancer (TNBC), colon cancer, colorectal cancer, glioma, head and neck squamous cell carcinoma, liver cancer, lymphoma, melanoma, prostate cancer, pancreatic cancer, renal cancer, or other solid tumors.

Intravesicular or Intravesical Dosages and Regimens

In an embodiment of intravesicular administration, or an embodiment of intravesical administration, E7766 or a pharmaceutically acceptable salt thereof is administered to a patient first in an induction cycle (Cycle 1) lasting 6 weeks. In the induction cycle E7766 or a pharmaceutically acceptable salt thereof is administered on days 1, 8, 15, 22, 29 and 36. Subsequent maintenance cycles (Cycle 2 and on) are initiated as identified in Table 1 below:

TABLE 1

| Cycle (week #/month #) | Days administered within cycle |
|---|---|
| Cycle 2 (Week 13, Month 3) | 1, 8 and 15 |
| Cycle 3 (Week 26, Month 6) | 1, 8 and 15 |
| Cycle 4 (Week 52, Month 12) | 1, 8 and 15 |
| Cycle 5 (Week 78, Month 18) | 1, 8 and 15 |
| Cycle 6 (Week 104, Month 24) | 1, 8 and 15 |

The total dose administered each time may be 600 μg, 800 μg, 1,600 μg, 2000 μg, 2,400 μg, 3,200 μg, 6,400 μg, 9600 μg, or 12,800 μg. The dose administered may be in one of the following dosage ranges: 800 μg to 12,800 μg; 800 μg to 9,600 μg; 800 μg to 6,400 μg; 800 μg to 3,200 μg; 800 μg to 2,400 μg; 800 μg to 2,000 μg; 800 μg to 1,600 μg; 1,600 μg to 12,800 μg; 1,600 μg to 9,600 μg; 1,600 μg to 6,400 μg; 1,600 μg to 3,200 μg; 1,600 μg to 2,400 μg; 1,600 μg to 2,000 μg; 2,000 μg to 12,800 μg; 2,000 μg to 9,600 μg; 2,000 μg to 6,400 μg; 2,000 μg to 3,200 μg; 2,000 μg to 2,400 μg; 2,400 μg to 12,800 μg; 2,400 μg to 9,600 μg; 2,400 μg to 6,400 μg; 2,400 μg to 3,200; 3,200 μg to 12,800 μg; 3,200 μg to 9,600 μg; 3,200 μg to 6,400 μg; 6,400 μg to 12,800 μg; 6,400 μg to 9,600 μg; or 9,600 μg to 12,800 μg. In another embodiment, E7766 or a pharmaceutically acceptable salt thereof is provided as a solid or concentrated solution and diluted in normal saline to a final volume of 25 mL for intravesicular administration. In another embodiment, E7766 or a pharmaceutically acceptable salt thereof is provided as a solid or concentrated solution and diluted in normal saline to a final volume of 25 mL for intravesical administration.

In an embodiment, E7766 or a pharmaceutically acceptable salt thereof is provided as an intravesicular administration for treatment of cancer (including muscle invasive and non-muscle invasive bladder cancer (NMIBC, including *Bacillus* Calmette-Guerin (BGC) Therapy unresponsive NMIBC), transitional cell carcinoma of the bladder, Ta or T1 papillary disease with or without carcimoa in situ (CIS), and urinary bladder neoplasms). In an embodiment, E7766 or a pharmaceutically acceptable salt thereof is provided as an intravesical administration for treatment of bladder cancer (including muscle invasive and non-muscle invasive bladder cancer (NMIBC, including *Bacillus* Calmette-Guerin (BGC) Therapy unresponsive NMIBC), transitional cell carcinoma of the bladder, Ta or T1 papillary disease with or without carcimoa in situ (CIS), and urinary bladder neoplasms).

Dosage Forms: Release Properties

Sustained-release formulations can achieve a degree of sustained effect. However, the exposure and/or the bioavailability of the active ingredient may vary based on a variety of factors, such as for example, the absorption window, the carriers or excipients used in the formulation, the mode of delivery of the formulation, and/or the transit time of the active ingredient through the gastrointestinal tract of the patient.

A therapy can contain at least one sustained-release portion for performing a sustained-release function and one immediate release portion for performing an immediate release function. In certain embodiments, when the therapy is in a single dosage form, it can be in the form of tablets formed from a mixture of sustained-release granules constituting a sustained-release portion and immediate-release granules constituting an immediate-release portion, a capsule preparation obtained by filling a capsule with sustained-release granules and immediate-release granules, or press-coated tablets in which an outer layer constituting an immediate-release portion is formed on an inner core constituting a sustained-release portion. There is, however, no limitation to the above embodiments.

Moreover, there are no particular limitations on the state of containment of the drug in the composition or in an immediate-release portion or a sustained-release portion; the compound may be dispersed uniformly in the composition, immediate release portion or sustained release portion, or may be contained in only one part of the composition, immediate-release portion or sustained-release portion, or may be contained such that there is a concentration gradient.

A sustained-release portion in the composition according to the present invention can contain at least one non-pH-dependent polymeric substance or pH-dependent polymeric substance for controlling drug release.

A non-pH-dependent polymeric substance used herein can comprise a polymeric substance whose charge state hardly changes under pH conditions generally found in the gastrointestinal tract, specifically from pH 1 to pH 8. This means, for example, a polymeric substance that does not have functional groups whose charge state changes depending on the pH such as basic functional groups such as amino groups or acidic functional groups such as carboxylic acid groups. Note that the non-pH-dependent polymeric substance can be included for giving the composition according to the present invention a sustained-release function, but may also be included for another purpose. Moreover, the non-pH-dependent polymeric substance used in the present invention may be water-insoluble, or may swell in water or dissolve in water to form a gel.

Examples of water-insoluble non-pH-dependent polymeric substances include, but are not limited to, cellulose ethers, cellulose esters, and methacrylic acid-acrylic acid copolymers (trade name Eudragit, manufactured by Rohm GmbH & Co. KG, Darmstadt, Germany).

Examples include, but are not limited to, cellulose alkyl ethers such as ethylcellulose (trade name Ethocel, manufactured by Dow Chemical Company, USA), ethyl methylcellulose, ethyl propylcellulose or isopropylcellulose, and butylcellulose, cellulose aralkyl ethers such as benzyl cellulose, cellulose cyanoalkyl ethers such as cyanoethylcellulose, cellulose organic acid esters such as cellulose acetate butyrate, cellulose acetate, cellulose propionate or cellulose butyrate, and cellulose acetate propionate, ethyl acrylate-methyl methacrylate copolymers (trade name Eudragit NE, manufactured by Rohm GmbH & Co. KG, Darmstadt, Germany), and aminoalkyl methacrylate copolymer RS (trade names Eudragit RL, Eudragit RS).

There are no particular limitations on the mean particle diameter of a water-insoluble polymer used in the present invention, but usually the lower this mean particle diameter the better the performance, with the mean particle diameter preferably being from 0.1 to 100 μm, more preferably from 1 to 50 μm, particularly preferably from 3 to 15 μm, most preferably from 5 to 15 μm. Moreover, examples of water-soluble or water-swelling non-pH-dependent polymeric substances include, but are not limited to, polyethylene oxide (trade name Polyox, manufactured by Dow Chemical Company, molecular weight 100,000 to 7,000,000), low-substituted hydroxypropyl cellulose (trade name L-HPC, manufactured by Shin-Etsu Chemical, Japan), hydroxypropyl cellulose (trade name HPC, manufactured by Nippon Soda, Co., Ltd, Japan), hydroxypropyl methylcellulose (trade names Metolose 60SH, 65SH, 90SH, manufactured by Shin-Etsu Chemical, Japan), and methylcellulose (trade name Metolose SM, manufactured by Shin-Etsu Chemical, Japan).

In some embodiments a single non-pH-dependent polymeric substance may be contained in the composition, or a plurality of the non-pH-dependent polymeric substances may be contained. The non-pH-dependent polymeric substance, if used in embodiments reported herein, may be a water-insoluble polymeric substance, more preferably ethylcellulose, an ethyl acrylate-methyl methacrylate copolymer (trade name Eudragit NE), or an aminoalkyl methacrylate copolymer RS (trade name Eudragit RL, Eudragit RS). Particularly preferable is at least one of ethylcellulose and an aminoalkyl methacrylate copolymer RS. Most preferable is ethylcellulose. There are no particular limitations on the amount of the non-pH-dependent polymeric substance contained in the composition; this amount can be adjusted as appropriate in accordance with the purpose such as controlling sustained drug release.

A pH-dependent polymeric substance that can be used in embodiments reported herein may be a polymeric substance whose charge state changes under pH conditions generally found in the gastrointestinal tract, specifically from pH 1 to pH 8. This means, for example, a polymeric substance having functional groups whose charge state changes depending on the pH such as basic functional groups such as amino groups or acidic functional groups such as carboxylic acid groups. The pH-dependent functional groups of the pH-dependent polymeric substance are preferably acidic functional groups, with the pH-dependent polymeric substance most preferably having carboxylic acid groups.

A pH-dependent polymeric substance used in the present invention may be water-insoluble, or may swell in water or dissolve in water to form a gel. Examples of pH-dependent polymeric substances used in the present invention include, but are not limited to, enteric polymeric substances. Examples of enteric polymeric substances include, but are not limited to, methacrylic acid-methyl methacrylate copolymers (Eudragit L100, Eudragit S100, manufactured by Rohm GmbH & Co. KG, Darmstadt, Germany), methacrylic acid-ethyl acrylate copolymers (Eudragit L100-55, Eudragit L30D-55, manufactured by Rohm GmbH & Co. KG, Darmstadt, Germany), hydroxypropyl methylcellulose phthalate (HP-55, HP-50, manufactured by Shin-Etsu Chemical, Japan), hydroxypropyl methylcellulose acetate succinate (AQOAT, manufactured by Shin-Etsu Chemical, Japan), carboxymethyl ethylcellulose (CMEC, manufactured by Freund Corporation, Japan), and cellulose acetate phthalate.

Examples of pH-dependent polymeric substances that swell in water or dissolve in water to form a gel include, but are not limited to, alginic acid, pectin, carboxyvinyl polymer, and carboxymethyl cellulose. In the present invention, a single pH-dependent polymeric substance may be contained in the composition, or a plurality of pH-dependent polymeric substances may be contained. The pH-dependent polymeric substance used in the present invention is preferably an enteric polymeric substance, more preferably a methacrylic acid-ethyl acrylate copolymer, a methacrylic acid-methyl methacrylate copolymer, hydroxypropyl methylcellulose phthalate, or hydroxypropyl methylcellulose acetate succinate, particularly preferably a methacrylic acid-ethyl acrylate copolymer.

When using a pH-dependent polymeric substance in the manufacturing process of a composition according to the present invention, a commercially available product of a powder type or a granular type, or a suspension type in which the pH-dependent polymeric substance has been dispersed in a solvent in advance can be used as is, or such a commercially available product can be used dispersed in water or an organic solvent. The lower the particle diameter of the pH-dependent polymeric substance the better the performance, with the pH-dependent polymeric substance preferably being of the powder type. In the case of a methacrylic acid-ethyl acrylate copolymer, an example is Eudragit L100-55. There are no particular limitations on the mean particle diameter of a pH-dependent polymeric substance used in the present invention, but the mean particle diameter is preferably from 0.05 to 100 μm, more preferably from 0.05 to 70 μm, most preferably from 0.05 to 50 μm. Moreover, there are no particular limitations on the amount of the pH-dependent polymeric substance, for example, in the case of an enteric polymeric substance, the amount is generally from 0.1 to 90 parts by weight, preferably from 1 to 70 parts by weight, more preferably from 5 to 60 parts by weight, particularly preferably from 10 to 50 parts by weight, based on 100 parts by weight of the composition.

A therapy according to embodiments reported herein may further contain any of various additives, such as any of various pharmacologically acceptable carriers such as diluents, lubricants, binders and disintegrants, as well as preservatives, colorants, sweeteners, plasticizers, film coating agents and so on, as necessary. Examples of diluents include, but are not limited to, lactose, mannitol, dibasic calcium phosphate, starch, pregelatinized starch, crystalline cellulose, light silicic anhydride, synthetic aluminum silicate, magnesium aluminate metasilicate or the like. Examples of lubricants include, but are not limited to, magnesium stearate, calcium stearate, talc, sodium stearyl fumarate or the like. Examples of binders include, but are not limited to, hydroxypropyl cellulose, methylcellulose, sodium carboxymethyl cellulose, hydroxypropyl methylcellulose, polyvinylpyrrolidone or the like. Examples of disintegrants include, but are not limited to, carboxymethyl cellulose, calcium carboxymethyl cellulose, croscarmellose sodium, sodium carboxymethyl starch, low-substituted hydroxypropyl cellulose or the like.

Examples of preservatives include, but are not limited to, paraoxybenzoic acid esters, chlorobutanol, benzyl alcohol, phenethyl alcohol, dehydroacetic acid, sorbic acid or the like. Preferable examples of colorants include, but are not limited to, water-insoluble lake pigments, natural pigments (e.g., beta-carotene, chlorophyll, red ferric oxide), yellow ferric oxide, red ferric oxide, black ferric oxide or the like. Preferable examples of sweeteners include, but are not limited to, sodium saccharin, dipotassium glycyrrhizate, aspartame, *stevia* or the like. Examples of plasticizers include, but are not limited to, glycerol fatty acid esters, triethyl citrate, propylene glycol, polyethylene glycol or the like. Examples of film coating agents include, but are not limited to, hydroxypropyl methylcellulose, hydroxypropyl cellulose or the like.

Manufacturing Methods

To manufacture embodiments as reported herein, a single conventional method, or a combination of conventional methods, can be used. For example, when manufacturing drug-containing granules as a sustained-release portion or an immediate-release portion, granulation is the main operation, but this may be combined with other operations such as mixing, drying, sieving, and classification. As the granulation method, for example, a wet granulation method in which a binder and a solvent are added to the powder and granulation is carried out, a dry granulation method in which the powder is compressed and granulation is carried out, a molten granulation method in which a binder that melts on heating is added and heating and granulation are carried out, or the like can be used.

Furthermore, in accordance with the granulation method, an operating method such as a mixing granulation method using a planetary mixer, a screw mixer or the like, a high-speed mixing granulation method using a Henschel mixer, a Super mixer or the like, an extruding granulation method using a cylindrical granulator, a rotary granulator, a screw extruding granulator, a pellet mill type granulator or the like, a wet high-shear granulation method, a fluidized-bed granulation method, a compression granulation method, a crushing granulation method, or a spraying granulation method can be used. After the granulation, drying using a dryer, a fluidized bed or the like, cracking, and sieving can be carried out to obtain the granules or fine granules for use. Moreover, a granulation solvent may be used when preparing the composition according to the present invention. There are no particular limitations on such a granulation solvent, which may be water or any of various organic solvents, for example, water, a lower alcohol such as methanol or ethanol, a ketone such as acetone or methyl ethyl ketone, methylene chloride, or a mixture thereof.

For sustained-release granules contained in embodiments, at least one drug and at least one selected from non-pH-dependent polymeric substances and pH-dependent polymeric substances are mixed together, a diluent and a binder are added as necessary, and granulation is carried out to obtain granular matter. The granular matter obtained is dried using a tray dryer, a fluidized bed dryer or the like, and sieving is carried out using a mill or an oscillator, whereby the sustained-release granules can be obtained. Alternatively, as a method of manufacturing sustained-release granules in the present invention, it is possible to add at least one drug, at least one selected from non-pH-dependent polymeric substances and pH-dependent polymeric substances, and as necessary a diluent and a binder using a dry compactor such as a roller compactor or a slug tabletting machine, and carry out compression-molding while mixing, and then carry out granulation by cracking down to a suitable size. The granular matter prepared using such a granulator may be used as is as granules or fine granules according to the present invention, or may be further cracked using a power mill, a roll granulator, a rotor speed mill or the like, and sieved to obtain sustained-release granules. Note that immediate-release granules can also be manufactured as for the sustained-release granules.

A compression-molded product can be manufactured as a drug-containing sustained-release portion or immediate-release portion, or as a composition reported herein using a single conventional method, or a combination of conventional methods. For example, at least one drug, at least one selected from non-pH-dependent polymeric substances and pH-dependent polymeric substances, a diluent such as mannitol or lactose, a binder such as polyvinylpyrrolidone or crystalline cellulose, a disintegrant such as carmellose sodium or crospovidone, and a lubricant such as magnesium stearate or talc are used, and tableting is carried out using an ordinary method, whereby the compression-molded product can be obtained. In this case, tabletting is the main operation in the method of manufacturing the compression-molded product, but this may be combined with other operations such as mixing, drying, sugar coating formation, and coating.

Examples of the method for the tabletting include, but are not limited to, direct compression molding in which at least one drug and pharmacologically acceptable additives are mixed together and then the mixture is directly compression-molded into tablets using a tabletting machine, and dry granule compression or wet granule compression in which sustained-release granules or immediate-release granules according to the present invention are subjected to compression-molding after adding a lubricant or a disintegrant as necessary. There are no particular limitations on the tabletting machine used in the compression molding; for example, a single-punch tabletting machine, a rotary tabletting machine, or a press-coated tabletting machine can be used.

Drug-containing sustained-release granules or immediate-release granules, or compression-molded product according to embodiments herein can be used as is in the form of granules or a tablet as the composition, but may also be subjected to further processing to manufacture the composition. For example, the compression-molded product or granules can be given a film coating using a film base material such as ethylcellulose, casein, methylcellulose, hydroxypropyl methylcellulose, methacrylic acid copolymer L, cellulose acetate phthalate, shellac or the like, or given a sugar coating using a sugar coating liquid containing saccharose, sugar alcohol, gum arabic powder, talc or the like, thus producing film-coated tablets or sugar-coated tablets. One solvent in this coating technique may be purified water, but an organic solvent such as an alcohol, a ketone, an ether or a chlorinated hydrocarbon, or a mixture thereof can also be used. For example, ethanol, acetone, methylene chloride or the like can be used as an organic solvent. Moreover, as the coating apparatus, an apparatus ordinarily used in coating techniques for manufacturing medicines can be used, with examples including a spray coating apparatus in which the coating is carried out by spraying a coating liquid or the like, and a rotor fluidized bed granulator for layering.

In the case of manufacturing capsule preparations, capsule preparations can be manufactured by filling sustained-release granules or immediate-release granules as above, or mini-tablets into hard gelatin capsules or HPMC capsules using an automatic capsule filling machine. Alternatively, in the case of the preparations for per-tube administration or a dry syrup that is used mixed with water or the like when taken, sustained-release granules or immediate-release granules as above can be mixed with a thickener or a dispersant so as to disperse these granules, the mixture then being made into granules or tablets. Furthermore, a liquid or jelly can be made using water, and substances selected from dispersants, emulsifiers, thickeners, preservatives, pH adjustors, sweeteners, flavorings, fragrances and so on. However, with respect to other manufacturing methods, there are no limitations to the above.

As reported in more detail below, mechanistic in vivo and in vitro experiments determined 1) the rate determining step in the systemic clearance of Compound 1; 2) the relative contributions of transporters involved in the uptake and biliary clearance of Compound 1; and 3) potential drug-drug interactions associated with OATP1B1/1B3 in humans.

The pharmacokinetics and disposition of Compound 1 were studied in vivo in bile duct cannulated rats and dogs as well as in OATP1B1/1B3 humanized mice. The transporter phenotyping of Compound 1 was conducted using transfected cell lines and vesicles. The biliary excretion and uptake clearance of Compound 1 was also determined in sandwich cultured human hepatocytes. In silico modeling, in particular simCYP™, was also used for physiologically based pharmacokinetic (PBPK) modeling and clinical drug-drug interaction (DDI) prediction. PBPK modeling was applied to evaluate potential drug-drug interactions with OATP inhibitors in the clinic.

Based on studies reported here, E7766 or a pharmaceutically acceptable salt thereof, and in particular Compound 1 may give rise to a potential drug-drug interaction with OATP inhibitors. Those OATP inhibitors may be OATP1B1 inhibitors and/or OATP1B3 inhibitors. Co-administration of OATP inhibitors with E7766 or a pharmaceutically acceptable salt thereof could alter dosage amounts and schedules for administration of E7766 or a pharmaceutically acceptable salt thereof and/or administration of an OATP inhibitor or could caution against the co-administration entirely.

OATP inhibitors that may have potential drug-drug interaction with E7766 or a pharmaceutically acceptable salt thereof may include, for example, but are not limited to fimasartan, clarithromycin, rifampin, clopidogrel, eslicarbazepine, CP-778875, isavuconazole, itraconazole, ombitasvir, asunaprevir, boceprevir, daclatasvir, dasabuvir, elbasvir, faldaprevir, glecaprevir, grazoprevir, letermovir, ombitasvir, paritaprevir, pibrentasvir, trimethoprim, ritonavir, simeprevir, sofosbuvir, telaprevir, velpatasvir, voxilaprevir, lopinavir, peficitinib, quercetin, tipranavir, metformin, diltiazem, sacubitril, valsartan, furosemide, gemfibrozil, eluxadoline, cyclosporine, tacrolimus, eltrombopag, grapefruit juice, ursodeoxycholic acid, milk thistle (*Silybum marianum*), emtricitabine, tenofovir, vercirnon (GSK1605786), telmisartan, epigallocatechin gallate, ezetimibe, amlodipine, obeticholic acid, omega-3 carboxylic acids, idelalisib, baicalin, empagliflozin, elvitegravir and cobicistat. OATP inhibitors are reported, in general, in Karlgren, et al., "Classification of Inhibitors of Hepatic Organic Anion Transporting Polypeptides (OATPs): Influence of Protein Expression on Drug-Drug Interactions," *J Med Chem,* 2012 May 24; 55(10): 4740-4763, which is incorporated by reference herein.

A system is disclosed that provides information on potential drug-drug interactions of E7766 or a pharmaceutically acceptable salt thereof and at least one OATP inhibitor. By making this information available concurrently with E7766 or a pharmaceutically acceptable salt thereof or a pharmaceutical composition comprising E7766 or a pharmaceutically acceptable salt thereof, potential drug-drug interactions (including possible clinical adverse events) may be managed. Management may occur, for example, by altering dosage amount, type, or schedule for the OATP inhibitor and/or E7766 or a pharmaceutically acceptable salt thereof, or by ceasing administration of either E7766 or a pharmaceutically acceptable salt thereof or the OATP inhibitor.

In some embodiments management of a potential drug-drug interaction occurs by reducing the amount of OATP inhibitor that is administered and/or the frequency of administration of the OATP inhibitor. In some embodiments management of a potential drug-drug interaction occurs by reducing the amount of E7766 or a pharmaceutically acceptable salt thereof or a pharmaceutical composition comprising E7766 or a pharmaceutically acceptable salt thereof that is administered and/or by reducing the frequency of administration of E7766 or a pharmaceutically acceptable salt thereof or a pharmaceutical composition comprising E7766 or a pharmaceutically acceptable salt thereof.

So that embodiments described herein may be more fully understood, the following examples are set forth. It should be understood that these examples are for illustrative purposes only and are not to be construed as limiting.

EXAMPLES

Methods and Materials

Compound 1 was formulated in sterile phosphate-buffered saline (PBS) for rat and dog studies and in 0.5% 0.1 N HCl, 5% DMSO, 10% EtOH, 84.5% saline for studies in WT and humanized mice. Rifampin was formulated in 0.5% 0.1 N HCl, 5% DMSO, 10% EtOH, 84.5% saline. Blank urine and bile, as well as plasma containing sodium heparin as the anticoagulant, were purchased from BioreclamationIVT (Westbury, N.Y.). Blank feces was obtained from rats purchased from Charles River Laboratories (Wilmington, Mass.).

Mass Spectrometry and HPLC conditions for the analysis of Compound 1 in biological matrices are shown below.

into collection tubes cooled via an ice pack. Feces samples for rats were collected over 0 to 24 hour interval. All samples were transferred into properly labeled tubes and stored at −70° C. until pending shipment to the bioanalytical facility. All samples were analyzed using LC-MS/MS and the pharmacokinetic parameters of Compound 1 were determined with Phoenix WinNonlin using non-compartmental analysis. Table 2 shows percent of administered dose excreted (% Ae) in bile, urine, or feces of bile duct cannulated rat or dog following intravenous administration of 1 mg/kg or 0.075 mg/kg respectively. Data are shown as Mean SD. NC indicates Not Collected.

TABLE 2

| Species | % Ae, bile | % Ae, urine | % Ae, feces |
|---------|-----------|-------------|-------------|
| Rat | 92.1 ± 7.3 | 13.7 ± 2.8 | 0.4 ± 0.2 |
| Dog | 87.9 ± 30.5 | 5.0 ± 4.4 | NC |

| Analyte | Compound 1 | | | |
|---------|-----------|---|---|---|
| Chromatography Settings: | | | | |
| Column Type | Waters XBridge Oligonucleotide BEH C18 column, 130 Å, 2.5 μm (4.6 mm inner diameter × 50 mm length) | | | |
| Mobile Phase | A: 2 mmol/L ammonium bicarbonate in 95:5 H2O:MeOH (v:v) B: 2 mmol/L ammonium bicarbonate in 95:5 MeOH:H₂O (v:v) | | | |
| | Time (min) | Flow (μL/min) | A % | B % |
| HPLC Gradient | 0.0 | 500 | 100 | 0 |
| | 0.3 | 500 | 100 | 0 |
| | 3.0 | 500 | 0 | 100 |
| | 5.0 | 500 | 0 | 100 |
| | 5.2 | 500 | 100 | 0 |
| | 9.0 | 500 | 100 | 0 |
| Injection Volume | 10 μL | | | |
| Retention Time | approximately 3.90 min | | | |
| Mass Spectrometer Settings: | | | | |
| Precursor Ion (m/z) | 372.4 $(M-2H)^{2-}$ | | | |
| Product Ion (m/z) | 186.5 | | | |
| Declustering potential (V) | −65 | | | |
| Collision energy (V) | −38 | | | |
| CXP (V) | −12 | | | |
| Entrance potential (V) | −10 | | | |
| Dwell time (ms) | 300 | | | |
| CAD | 10 | | | |
| Curtain gas | 20 | | | |
| Gas 1 | 60 | | | |
| Gas 2 | 80 | | | |
| Ionspray voltage (V) | −4500 | | | |
| Temperature (° C.) | 550 | | | |
| Q1 resolution | Unit | | | |
| Q3 resolution | Unit | | | |
| CEM (V) | 2300 | | | |
| Deflector | 75 | | | |

Example 1: Pharmacokinetics in Rat and Dog

Male bile duct-cannulated beagle dogs or Sprague Dawley rats (n=3) were given a single intravenous (IV) dose of Compound 1. Plasma, urine and bile samples were collected from the dogs, and blood, urine, bile and feces samples were collected from rats up to 48 hours post-dose. Blood samples were kept on wet ice after collection until centrifuged for separation of plasma. Urine samples were collected at intervals 0 to 4, 4 to 8, 8 to 24, and 24 to 48 hours post-dose into collection tubes on wet ice. Bile samples were collected at intervals 0 to 4, 4 to 8, 8 to 24, and 24 to 48 hours post-dose

Example 2: Pharmacokinetics in Knockout, Humanized and Wild-Type Mice

Age-matched Oatp1a/1b cluster-knockout, OATP1B1- or OATP1B3-knockin mice humanized on the Oatp1a/1b-knockout background, and wild-type FVB male mice were purchased from Taconic Biosciences (Hudson, N.Y., USA). Mice were between 8 and 10 weeks of age (22-34 g) at the time of study. Compound 1 was administered at a dose of 0.5 mg/kg coadministered with either vehicle or rifampin (30 mg/kg). Blood and liver samples were collected at 0.083, 0.25, 0.5, 1, 1.5, 3, 6 hours. Plasma was isolated from blood samples by centrifugation. All samples were stored at −80° C. until bioanalysis.

Compound 1 was dosed via intravenous administration to WT, humanized, and KO mice. Blood, urine, and feces were collected from the animals over 6 hours. Blood spots were collected and expelled FTA™ DMPK-B DBS Card (GE Healthcare, Life Sciences, Whatman™) within the appropriate sample circle. Pharmacokinetics of Compound 1 in WT animals was also assessed after co-administration with rifampin. Liver samples were also collected from WT animals and frozen until analysis. All samples were analyzed using LC-MS/MS and the pharmacokinetics parameters of Compound 1 were determined with Phoenix WinNonlin using non-compartmental analysis.

In Vivo PK of Compound 1 in Oatp1b2 Knockout and OATP1B Humanized Mice

Figure 2A:
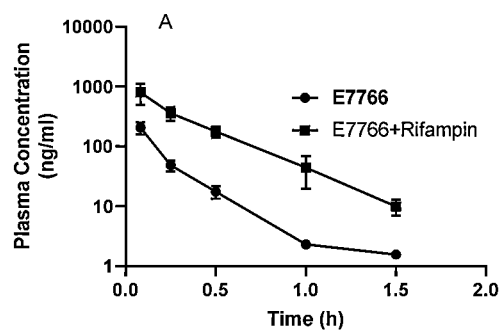
FIG. 2A through FIG. 2C show in vivo PK profiles and elimination of Compound 1 with and without codosing of Rifampin ((7S,9E,11S,12R,13S,14R,15R,16R,17S,18S,19E, 21Z)-2,15,17,27,29-pentahydroxy-11-methoxy-3,7,12,14, 16,18,22-heptamethyl-26-{(E)-[(4-methylpiperazin-1-yl) imino]methyl}-6,23-dioxo-8,30-dioxa-24-azatetracyclo [23.3.1.14,7.05,28]triaconta-1(28),2,4,9,19,21,25(29),26-octaen-13-yl acetate).
Figure 2B:
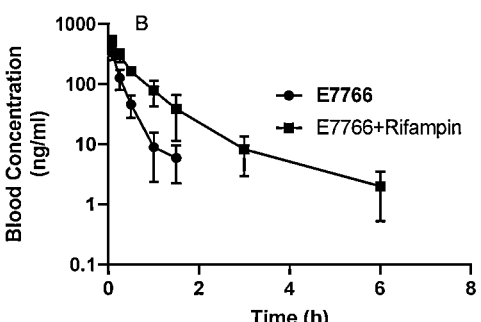
Figure 2C:
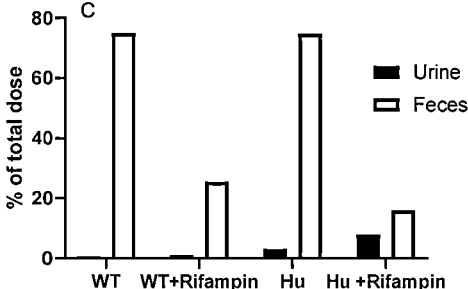

FIG. 2A through 2C show an in vivo PK profile and elimination of Compound 1 with and without a co-dose of the Oatp/OATP inhibitor Rifampin in different mouse models. FIG. 2A shows PK profile of Compound 1 and the co-dose with Rifampin in wild type mice. FIG. 2B shows PK profile of Compound 1 and the co-dose with Rifampin in OATP1Bs humanized mice. FIG. 2C shows excretion of Compound 1 into urine and feces for the mice of FIG. 2A and FIG. 2B.

Based on these results, we noted that co-dosing of the Oatp/OATP inhibitor Rifampin with Compound 1 increased system exposure of Compound 1 by 4.5 fold while decreasing biliary excretion by 66-79%. This indicates transporter-mediated uptake is rate determining for the clearance and for the disposition of Compound 1.

Figure 5:
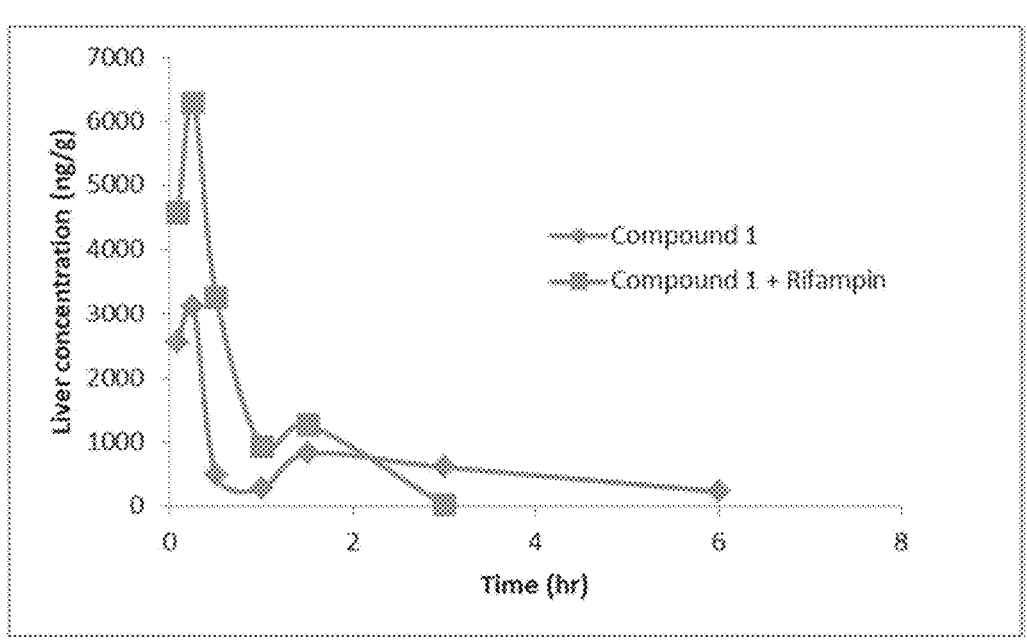
FIG. 5 shows AUC of Compound 1 in the liver of wild type mice following intravenous administration of Compound 1 and co-administration of Compound 1 and Rifampin.

Further review, shown in FIG. 5, shows AUC (area under the curve, or bioavailabilty) of Compound 1 in the liver following IV administration in wild type mice did not change significantly after coadministration with Rifampin. The Kp (liver/plasma) value of Compound 1 decreased 5-fold in the presence of Rifampin. $C_{max}$ of Compound 1 increased about 2-fold in the presence of rifampin.

Example 3: Evaluation of Uptake and Biliary Excretion Using Sandwich Cultured Human Hepatocyte Assay Hepatic uptake and hepatobiliary disposition of Compound 1 was evaluated in sandwich-cultured human hepatocytes (SCHH) prepared from one donor, JEL. For assessing hepatic uptake, Compound 1 was incubated for 1, 5, and 10 minutes and the solutions were collected and frozen at −80° C. until process for bioanalysis. The wells were then washed three times with ice cold Plus (+) Buffer and were frozen at −80° C. until processed for bioanalysis. Biliary excretion of compound 1 was assessed in SCHH utilizing B-CLEAR® Technology. Briefly, cell culture medium was removed, and hepatocytes were washed twice with warm Plus (+) or Minus (−) Buffer to maintain or disrupt tight junctions, respectively. The wash solutions were removed and replaced with fresh Plus (+) Buffer or Minus (−) Buffer. The hepatocytes were conditioned for 10 minutes at 37° C. The conditioning solutions were removed and replaced with dosing solutions for Compound 1. Following a 20 minute incubation, the solutions were collected and frozen at −80° C. until process for bioanalysis. The wells were then washed three times with ice cold Plus (+) Buffer. The plates were frozen at −80° C. until processed for bioanalysis. The biliary excretion index (BEI) was calculated according to following equation:

$$BEI = 100 \times \frac{\text{Bile Accumulation}}{\text{Total Accumulation}_{Plus(+) Buffer}}$$

Figure 4A:
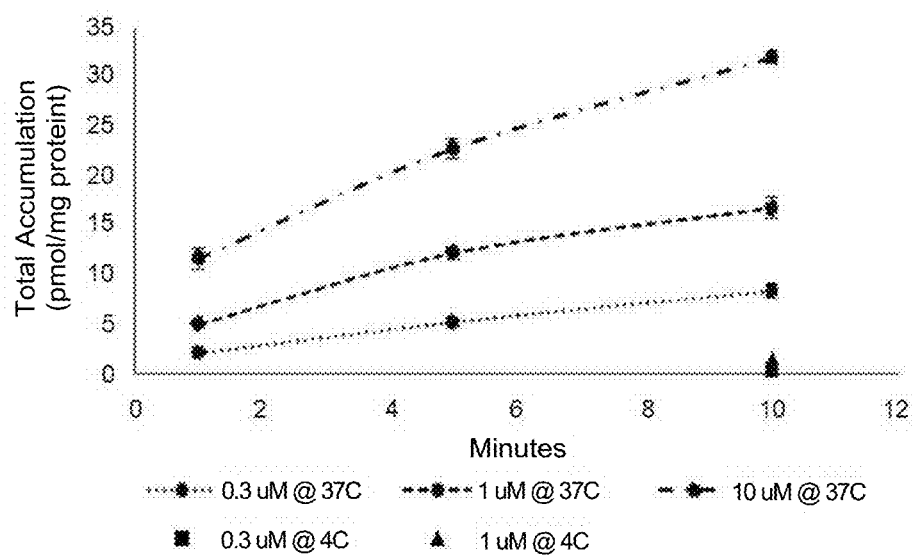
FIG. 4A shows hepatic uptake of Compound 1 in sandwich-cultured human hepatocytes (SCHH) over time.
Figure 4B:
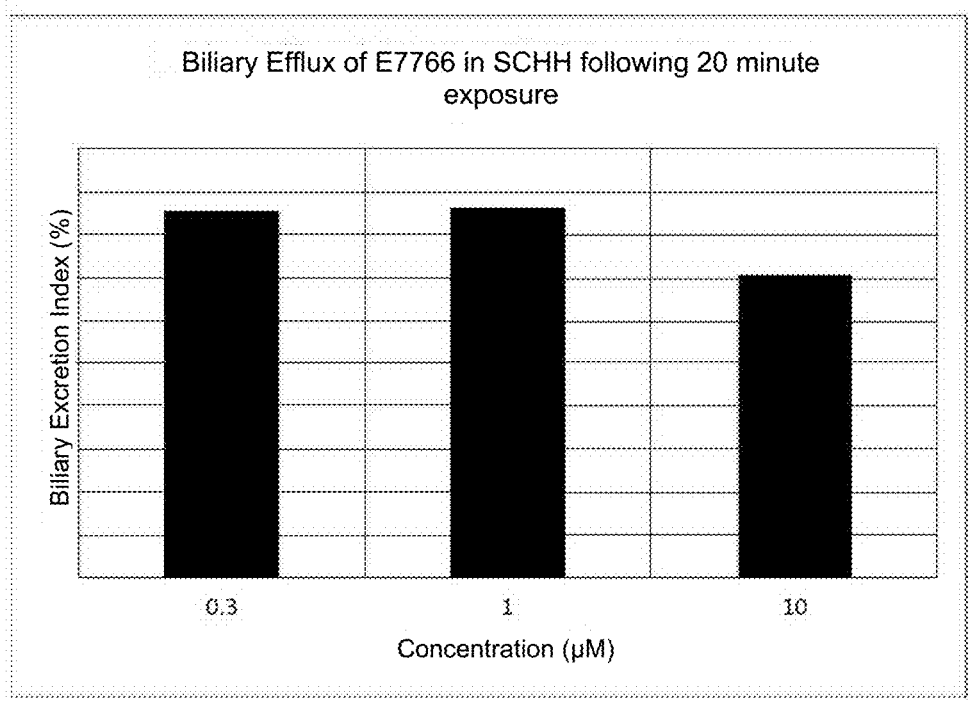
FIG. 4B shows biliary efflux of Compound 1 in SCHH following 20 minutes of exposure.

Hepatic uptake of Compound 1 was markedly decreased to <7.7% of 37° C. following incubations at 4° C. These results suggested that hepatic uptake of Compound 1 was primarily mediated by active uptake mechanisms. Hepatic uptake of Compound 1 was approximately dose-proportional from 0.3 to 1 μM dose levels following 1 to 5 minutes of exposure. However, this dose proportionality was lost at a concentration of 10 μM, suggesting hepatic uptake was saturated at concentrations >1 μM. The biliary excretion index (BEI) of Compound 1 ranged from 70.9 to 86.2% across the concentration range assessed, indicating a high biliary efflux for this compound. Results are shown in FIG. 4A and FIG. 4B.

Example 4: In Vitro Hepatobiliary Transporter Phenotyping—Evaluation of Transport in Overexpressed Cells or Vesicles TransportoCells™ (Corning, N.Y., USA) expressing OATP2B1, NTCP, and HEK293-FT cells stably transfected with the vector containing OATP1B1 cDNA or OATP1B3 cDNA or empty vector were grown in a Dulbecoo's modified Eagle's medium fortified with 10% fetal calf serum and 2 mmol/L sodium butyrate (for NTCP only) in a humidified incubator at 37° C. and 5% CO2. Cells were harvested at 90% confluence and then seeded in poly-D-lysine-coated 24-well 24 h prior to transporter assay. Cells were washed twice and pre-incubated with 200 μL of pre-warmed Krebs-Henseleit buffer. After pre-incubation, cells were incubated with 3 or 10 μmol L-1 of Compound 1 in presence or absence of 100 μmol L-1 of inhibitors (Rifamycin SV for OATP2B1, Troglitazone for NTCP, Rifamycin for OATP1B1 and OATP1B3). The transport reaction was terminated by aspirating the buffer from the wells at designated time. After washing three times with 200 μL of ice-cold Krebs-Henseleit buffer, the cells were lysed and the resulting cellular lysates were analyzed by LC-MS/MS.

Concentration-dependent uptake of Compound 1 via OATP1B1 and OATP1B3 were conducted with a concentration range of 0.25-100 μmol L-1 under linear uptake. All experiments were run in triplicates.

To study the interaction of Compound 1 with hepatic efflux (ABC) transporters, TransportoCells™ membrane vesicles expressing BCRP, BSEP, MRP2, and control vector vesicles were pre-incubation with vesicle uptake buffer (47 mmol L-1 MOPs-Tris, 65 mmol L-1 KCl, 7 mmol L-1 MgCl2, pH 7.4 for BCRP; 47 mmol L-1 MOPs-Tris, 2.5 mmol L-1 GSH, 65 mmol L-1 KCl, 7 mmol L-1 MgCl2, pH 7.4 for MRP2; and 10 mmol L-1 HEPES-Tris, 100 mmol L-1 KNO3, 12.5 mmol L-1 Mg(NO3)2, and 50 mmol L-1 sucrose, pH 7.4 for BSEP) at 37° C. for 10 minutes. The transport was initiated by adding of pre-warmed 25 mmol/L MgATP, 3 μmol L-1 of Compound 1 in presence or absence of inhibitors (3 μmol L-1 of Novobiocin for BCRP, 100 μmol L-1 of MK-571 for MRP2, and 20 μmol L-1 of Ketoconazole for BSEP). The transport was terminated at designated time by adding 200 μL ice-cold vesicle uptake buffer. The complete content was then rapidly filtrated using multi-screen HTS vacuum manifold, followed by 5 washes and filtrations. The plate was allowed to dry completely and then placed onto a 96-well receiver plate. A 50 μL of elute solution (75% methanol containing the internal standard)

was added into each assay well followed by centrifugation at 2000 rpm for 5 minutes. This lysis-and-centrifugation procedure was repeated one more time to maximize compound extraction. The yield samples from two centrifugation were combined and analyzed by LC-MS/MS. All experiments were run in triplicates.

Figure 1B:
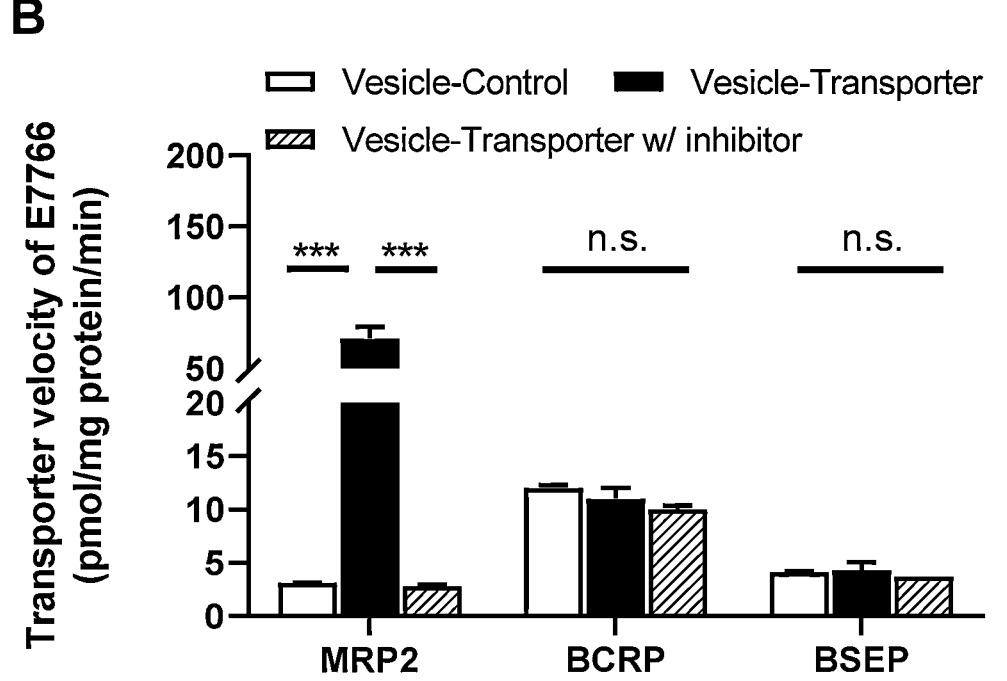

FIG. 1A through FIG. 1D show results of in vitro hepatobiliary transporter phenotyping studies of Compound 1. FIG. 1(A) shows uptake of Compound 1 evaluated on SLC transporter-expressing HEK293 cells; FIG. 1(B) shows transport of Compound 1 evaluated on ABC transporter-expressing membrane vesicles; FIG. 1(C) shows kinetic plot fitting and Michaelis-menten parameters of OATP1B1-mediated uptake of Compound 1; and FIG. (D) shows kinetic plot fitting and Michaelis-menten parameters of OATP1B3-mediated uptake of Compound 1. The results shown in FIG. 1A through FIG. 1D suggest that SLC transporters OATP1B1 and OATP1B3, and ABC transporter MRP2 are responsible for hepatic uptake and sequential biliary efflux of Compound 1.

Example 5: PBPK Modeling to Predict OATP1Bs-Mediated Drug-Drug Interaction of Compound 1 in Clinic PBPK modeling was conducted using the Simcyp™ in silico bottom-up PBPK modeling. PBPK modeling suggested that changes in systemic and hepatic exposure may occur if Compound 1 is coadministered with inhibitors of OATP1Bs. Furthermore, due to a predominant contribution of OATP1B3 but not OATP1B1 in hepatobiliary clearance of Compound 1, the hepatobiliary clearance of Compound 1 is unlikely to be subject to PK alteration due to polymorphism in PATP1B1.

Figure 3A:
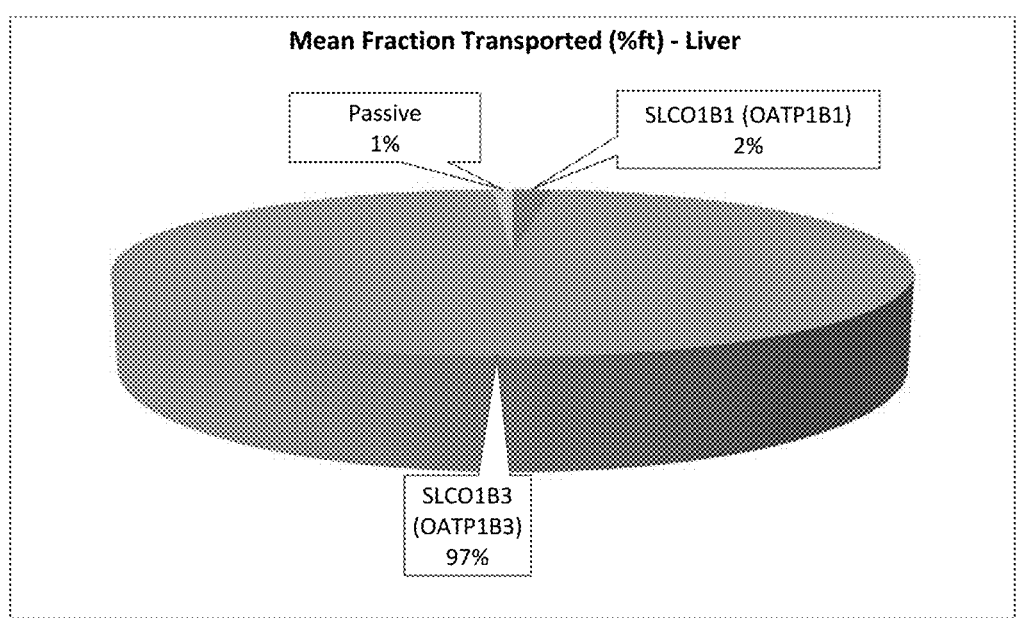
FIG. 3A shows the fraction transported by OATP1B1/ 1B3.
Figure 3B:
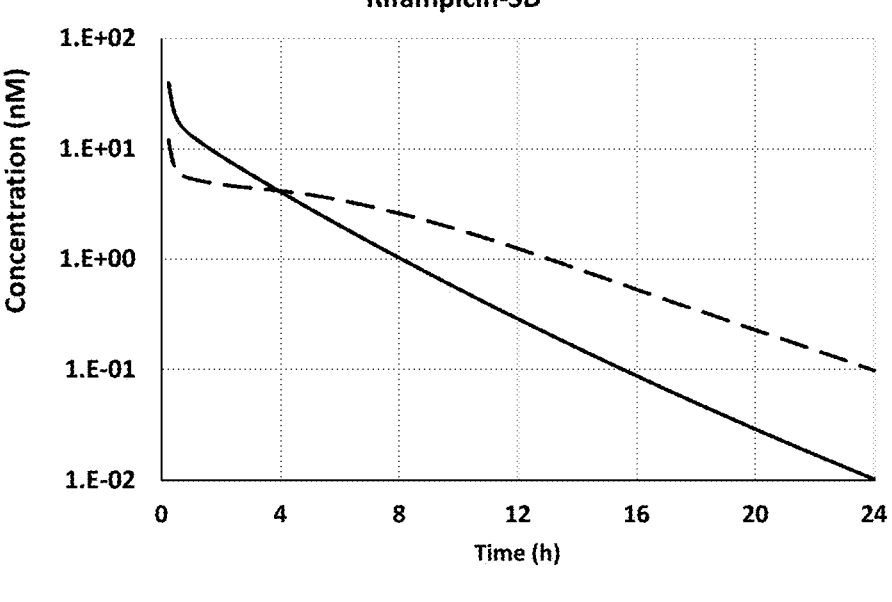
FIG. 3B, and FIG. 3C show the simulated liver and plasma concentrations of Compound 1 with or without coadministration with rifampicin.
Figure 3C:
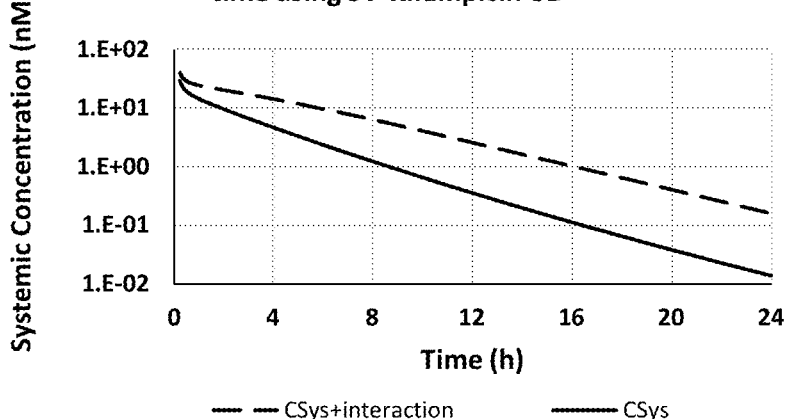
Figure 3D:
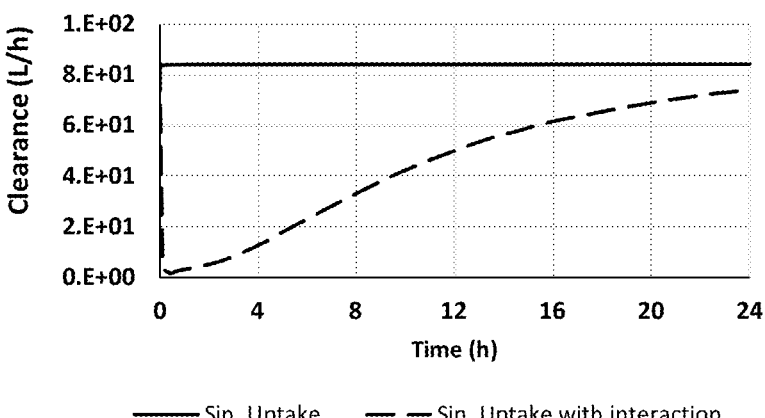
FIG. 3D shows mean values of sinusoidal uptake clearance of Compound 1 with and without interaction over time using rafampicin. Simulations were performed using a PBPK model developed with Simcyp™ modeling.

FIG. 4A shows mean fraction transported (ft %) of Compound 1 to the liver. FIG. 3B shows Mean Values of intra-liver concentration of Compound 1 with and without interaction with Rifampin over time. FIG. 3C shows mean values of systemic concentration in plasma of Compound 1 with and without interaction with Rifampin over time. FIG. 4D shows mean values of sinusoidal uptake clearance of Compound 1 with and without interaction with Rifampin over time. Simcyp™ software Version 17.0.0 was used. Simcyp™ parameters are shown below in Table 3.

TABLE 3

| Compound information | |
| --- | --- |
| Compound Name | Compound 1 |
| Version number | Not applicable |
| Molecule Type | Small Molecule |
| Route | iv |
| Dose Units | Dose (mg) |
| Dose | 1.000 |
| Start Day | 1.000 |
| Start Time | 9 h 0 m |
| Dosing Regimen | Single Dose |
| PhysChem and Blood Binding | |
| Mol Weight (g/mol) | 746.000 |
| log P | 1.310 |
| Compound Type | Monoprotic Acid |
| pKa 1 | 3.410 |
| B/P | 0.550 |
| Haematocrit | 45.000 |
| fu | 0.500 |
| Reference Binding Component | HSA |
| Protein Reference Conc (g/L) | 45.000 |
| % Bound to Lipoprotein | 0.000 |
| % Bound to Lipoprotein (CV %) | 0.000 |

TABLE 3-continued

| | |
| --- | --- |
| Distribution Model | Full PBPK Model |
| Vss input type | Predicted |
| Vss (L/kg) | 0.637 |
| Prediction Method | Method 2 (Rodgers et al) |
| log Po:w | 1.310 |
| logP vo:w input type | Predicted |
| logP vo:w Prediction Method | Hansch |
| logP vo:w Hansch a | 1.115 |
| logP vo:w Hansch b | −1.350 |
| logP vo:w | 0.111 |
| Compound Type | Monoprotic Acid |
| pKa 1 | 3.410 |
| Kp Scalar | 4.000 |
| Clearance Type | Enzyme Kinetics |
| Active Uptake into Hepatocyte | 1.000 |
| CL R (L/h) | 2.000 |
| Uptake Transport | |
| Organ/Tissue | Liver |
| Model | PerL |
| $CL_{PD}$ (mL/min/$10^6$ cells) | 0.00013 |
| Organ/Tissue | Liver |
| Jmax (pmol/min/million cells), OATP1B1 | 8.34 |
| Km (μM), OATP1B1 | 2.200 |
| fuinc, OATP1B1 | 1.000 |
| RAF/REF for OATP1B1 | 0.070 |
| Jmax (pmol/min/million cells), OATP1B3 | 24.39 |
| Km (μM), OATP1B3 | 4.000 |
| fuinc, OATP1B3 | 1.000 |
| RAF/REF for OATP1B3 | 0.800 |
| efflux CLint, T (μL/min/million cells) | 2.000 |
| fuinc | 1.000 |
| System | User |
| RAF/REF for efflux | 1.000 |
| Compound Name for inhibitor* | SV-Rifampicin-SD |
| Version number | 17.0.0 |
| Molecule Type | Small Molecule |
| Route | Infusion |
| Dose Units | Dose (mg) |
| Bolus Dose | 0.000 |
| Bolus Dosing Regimen | Single Dose |
| Infusion Dose | 600.000 |
| Infusion Duration (h) | 0.500 |
| Start Day | 1.000 |
| Start Time | 9 h 0 m |
| Dosing Regimen | Multiple Dose |
| Dose Interval (h) | 24.000 |
| Number of Doses | 1.000 |
| Trial Design | |
| Use Pop Representative | No |
| Population Size | 100.000 |
| Number of Trials | 10.000 |
| No of Subjects per Trial | 10.000 |
| Population name | Sim-Healthy Volunteers |
| Version number | 17.0.0 |
| Minimum Age (years) | 20.000 |
| Maximum Age (years) | 50.000 |
| Propn. of Females | 0.500 |
| Fix Individual Trial Design | No |
| Prandial State | Fasted |
| PKPD Parameters | On |
| PKPD Profiles | On |
| Start Day/Time | Day 1, 09:00 |
| End Day/Time | Day 2, 09:00 |
| Study Duration (h) | 24.000 |
| Sub: Route | iv |
| Inh 1: Route | Infusion |

*The simCYP built-in workspace for Rifampicin "SV-Rifampicin-SD" and parameters incorporated are used for DDI simulation Summary Pharmacokinetics in bile duct cannulated rat showed that Compound 1 was predominantly excreted unchanged in the bile (>800%) and to a minor extent in urine (<20%). Studies using sandwich cultured human hepatocytes showed temperature-dependent active uptake, followed by excretion into the bile pockets. Further in vitro studies confirmed that Compound 1 was a substrate of human OATP1B1, OATP1B3, and efflux transporter NIRP2. Plasma exposure of Compound 1 increased 4.5-fold in the presence of rifampin in humanized OATP1B1/1B3 mice. Phenotyping studies showed predominant contribution of OATP1B3 over OATP1B1 in the hepatobiliary clearance of Compound 1. Thus changes in systemic exposure due to polymorphisms in OATP1B1 are unlikely. PBPK modeling and simulation demonstrated potentially a two-fold elevation of systemic exposure of Compound 1 when co-medicated with inhibitors of OATP1B1/1B3.

We claim:

1. A method of preventing overexposure of E7766 or a pharmaceutically acceptable salt thereof in a patient selected for treatment with E7766 or a pharmaceutically acceptable salt thereof, comprising:
    monitoring an exposure of E7766 or a pharmaceutically acceptable salt thereof when the patient is being administered an OATP1B1 or OATP1B3 inhibitor, and
    maintaining said exposure to a value below 12,800 μg E7766 or a pharmaceutically acceptable salt thereof per 100 kg patient body weight.

2. The method of claim 1, comprising maintaining said exposure to a value below 9,600 μg E7766 or a pharmaceutically acceptable salt thereof per 100 kg patient body weight.

3. The method of claim 2, comprising maintaining said exposure to a value below 3,200 μg E7766 or a pharmaceutically acceptable salt thereof per 100 kg patient body weight.

4. The method of claim 3, comprising maintaining said exposure to a value below 2,000 μg E7766 or a pharmaceutically acceptable salt thereof per 100 kg patient body weight.

5. The method of claim 4, comprising maintaining said exposure to a value below 1,600 μg E7766 or a pharmaceutically acceptable salt thereof per 100 kg patient body weight.

6. The method of claim 5, comprising maintaining said exposure to a value below 800 μg E7766 or a pharmaceutically acceptable salt thereof per 100 kg patient body weight.

7. The method of claim 6, comprising maintaining said exposure to a value below 300 μg E7766 or a pharmaceutically acceptable salt thereof per 100 kg patient body weight.

8. The method of claim 7, comprising maintaining said exposure to a value below 75 μg E7766 or a pharmaceutically acceptable salt thereof per 100 kg patient body weight.

9. The method of claim 8, comprising maintaining said exposure to a value below 25 μg E7766 or a pharmaceutically acceptable salt thereof per 100 kg patient body weight.

10. The method of claim 1, wherein said maintaining comprises reducing a dosage of E7766 or a pharmaceutically acceptable salt thereof.

11. The method of claim 10, wherein said reducing comprises a reduction of the dosage of E7766 or a pharmaceutically acceptable salt thereof selected from the group consisting of 5%, 10%, 15%, 20%, 25%, 30%, 35%, 40%, 45%, 50%, 55%, 60%, 65%, 70%, 75%, 80%, 85%, 90%, and 95%.

12. The method according to claim 1 wherein said exposure is evaluated from said patient's blood plasma.

*   *   *   *   *